United States Patent [19]

McCall

[11] 4,331,819

[45] May 25, 1982

[54] WATER REMOVAL IN NITRATION OF AROMATIC HYDROCARBONS

[75] Inventor: Robert McCall, Newark, Del.

[73] Assignee: E. I. Du Pont de Nemours and Company, Wilmington, Del.

[21] Appl. No.: 143,372

[22] Filed: Apr. 24, 1980

[51] Int. Cl.³ .................. C07C 76/02; C07C 79/10
[52] U.S. Cl. ................................. 568/939; 568/927; 568/932; 568/936
[58] Field of Search ............... 568/927, 932, 933, 934, 568/935, 936, 937, 939, 940

[56] References Cited

U.S. PATENT DOCUMENTS

| | | | |
|---|---|---|---|
| 2,007,510 | 7/1935 | Thornton | 568/939 |
| 2,135,012 | 11/1938 | Meissner | 568/927 |
| 2,435,314 | 2/1948 | Kokatnur | 568/939 |
| 2,951,877 | 9/1960 | Kouba et al. | 568/935 |
| 3,204,000 | 8/1965 | Samuelsen | 568/935 |
| 3,371,122 | 2/1968 | Betschel | 568/940 |
| 3,415,876 | 12/1968 | Boomstra et al. | 568/937 |
| 3,928,475 | 12/1975 | Dassel | 568/939 |
| 3,957,889 | 5/1976 | Millinam et al. | 568/932 |
| 4,123,466 | 10/1978 | Lin et al. | 568/939 |

Primary Examiner—Teddy S. Gron

[57] ABSTRACT

The invention relates to a process for the preparation of nitrated aromatic compounds by the mixed acid process, in which water is removed from the reaction mass by passing an inert gas through it.

4 Claims, 1 Drawing Figure

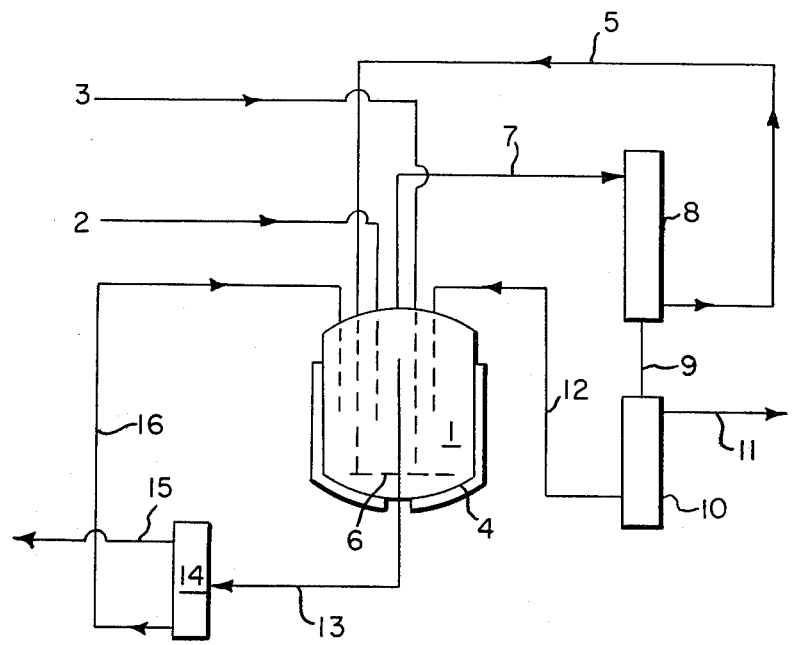

WATER REMOVAL IN NITRATION OF AROMATIC HYDROCARBONS

BACKGROUND OF THE INVENTION

1. Field of the Invention

This invention relates to the mixed acid process for nitrating aromatic hydrocarbons. It is more particularly directed to a procedure in that process for removing water from the reaction mass.

2. Description of the Prior Art

The nitration of aromatic hydrocarbons, especially benzene, is of great commercial importance. Although many nitration processes are known, the one most widely used is the continuous mixed acid nitration.

In that process, an aromatic hydrocarbon compound and nitric acid are brought together in a medium of concentrated sulfuric acid. The sulfuric acid acts on the nitric acid to form nitronium ion ($NO_2^+$), which is the actual nitrating agent.

The rate of reaction in the process is governed by the concentration of nitronium ions in the medium, higher concentrations of course giving faster nitration. The concentration of nitronium ions, in turn, is governed by the concentration of sulfuric acid in the medium. As the nitration proceeds, water is continuously brought into the medium with the nitric acid feed, and as a reaction product. This water dilutes the medium and lowers its sulfuric acid content to the point where the nitration reaction slows, or even stops.

It is therefore necessary to continuously remove water from the reaction medium to keep the sulfuric acid content at its optimum of about 70-75%, by weight, and thus maintain the reaction at maximum efficiency. The most common method of doing this is to continuously run the medium through a concentrator.

From a practical standpoint, this method of water removal is generally satisfactory, but recent emphasis on pollution control and energy conservation has made it less desirable because the method generates sulfuric acid mist which must be dealt with, and because large amounts of energy are required. Besides this, the concentrators are expensive because they must be made of materials strong enough to withstand constant exposure to the strong acid.

SUMMARY OF THE INVENTION

According to the invention, water can be removed from such a nitration reaction medium by passing an inert gas through it. As the gas flows through the medium, it becomes humidified and carries captured water with it as it leaves the reactor.

The principal advantages of this are (1) most of the energy needed for humidification of the gas comes from the heat of the reaction itself;
(2) expensive extrinsic drying equipment is not needed;
and
(3) air pollution in the form of sulfuric acid mist is minimized.

DETAILED DESCRIPTION OF THE INVENTION

The invention can be best understood by referring to the drawing, which is a flow sheet of the process of the invention.

Reactor 1 is charged with 60-70% sulfuric acid, and nitrated aromatic hydrocarbon of the kind to be produced, in an acid/hydrocarbon weight ratio of 50-60/40-50. Aromatic hydrocarbon and nitric acid (60-70%) are then continuously fed into the reactor through lines 2 and 3 to form a reaction mass having an aqueous phase and an organic phase. Examples of aromatic hydrocarbons which can be nitrated according to the process are benzene, toluene and chlorobenzene. Benzene is preferred.

The hydrocarbon and nitric acid are fed into the reactor at such rates and in such ratios to each other that, after reaction has begun, the aqueous phase contains, at any given time,

| | |
|---|---|
| sulfuric acid | 60-70%, by weight, preferably about 65% |
| nitric acid | 0.1-0.3%, preferably 0.2% |
| water | a complementary amount |
| and the organic phase contains | |
| aromatic hydrocarbon | 0.5-3%, preferably 1% |
| nitrated aromatic hydrocarbon | 97-99.5%, preferably 99%. |

The temperature of the reaction mass is held at 120°-140° C., preferably about 130° C., by heater 4 and is kept under a pressure of about 3450 pascals (gauge).

The gas is continuously fed into the reactor through line 5. This gas should be inert to the nitration reaction, contain as little oxygen as possible, and be capable of being humidified under the reaction conditions. Nitrogen, halogenated hydrocarbons, carbon dioxide and the inert atmospheric gases are examples. Nitrogen is preferred.

The gas is fed into the reactor at a temperature of 20°-60° C., preferably about 40°, and is bubbled through the medium by sparger 6 or other suitable means at the rate of 130-150 moles per hour, preferably 145 moles per hour. The gas rises through the reaction mass, is humidified by water extracted from the mass, and is then withdrawn from the reactor through line 7. At this point the gas stream contains, besides water, (a) nitrated product, (b) unreacted hydrocarbon and (c) unreacted nitric acid. Most of (a), (b) and (c) can be extracted from the gas stream by condenser 8, and the dried gas can be fed back to the reactor through line 5.

The condensate from the gas stream comprises water and an organic phase. If desired, this condensate can be fed via line 9 to separator 10, where the water and organic phase are separated. The water can be discarded through line 11, and the organic phase, which contains nitrated hydrocarbon and unreacted hydrocarbon, can be recycled to the reactor through line 12.

The reaction mass is continuously withdrawn from the reactor through line 13. At this point, the mass consists of an aqueous phase, mostly sulfuric acid and water, and an organic phase, principally nitrated hydrocarbon, with minor amounts of unreacted hydrocarbon and reaction byproducts. These phases can be separated in separator 14. The organic phase can be withdrawn through line 15 and conventionally purified to yield nitrated hydrocarbon product. The aqueous phase, mostly sulfuric acid and water, can be recycled to the reactor via line 16.

DESCRIPTION OF THE BEST MODE

In the following description, all parts are by weight.

Reactor 1 is charged with 26,600 parts of 70% sulfuric acid and 20,000 parts of nitrobenzene. Heat is applied with heater 4 and nitrogen is run into the charge through line 5 and sparger 6 at the rate of 2.3 cubic meters per minute (14.5 moles per hour) until the temperature of the charge is 130° C. The nitrogen flow is then increased to 23 cubic meters per minute (145 moles per hour) and the benzene and nitric acid feeds are started and held at the rates of 3244 and 4122 parts per hour, respectively.

The gas stream, taken from the reactor through line 7, consists of nitrogen and 20% by weight of water, the remainder being nitrobenzene, benzene and nitric acid. The gas stream is fed to condenser 8; the dried gas is fed back to the reactor through line 5. The condensate is separated in separator 10; the aqueous phase is discarded and the organic phase is recycled through line 12.

The reaction medium, consisting of

| | | |
|---|---|---|
| nitrobenzene | 5000 | parts |
| benzene | 50.5 | |
| dinitrophenol | 17.3 | |
| water | 2370 | |
| sulfuric acid | 4452 | |
| nitric acid | 23.7 | | is continuously withdrawn from the reactor through line 13 and is then passed through separator 14. The aqueous phase is recycled to the reactor via line 16 and the organic phase is conventionally purified to give product nitrobenzene.

INDUSTRIAL APPLICABILITY

The process of the invention can be used to prepare nitrobenzene, useful as an intermediate in the preparation of aniline and other commodity chemicals.

What is claimed is:

1. In the continuous process of nitrating an aromatic hydrocarbon in which the hydrocarbon, preformed nitric acid and 60–70% sulfuric acid are brought together to form a reaction mass, the improvement comprising removing enough water from the reaction mass to maintain the sulfuric acid strength at about 60–70% by bringing the mass into intimate contact with a gas, inert to the nitration reaction and capable of being humidified under the reaction conditions, thus humidifying the gas, and then removing the gas from the reaction zone.

2. The process of claim 1 in which the gas is nitrogen or carbon dioxide.

3. The process of claim 2 in which the aromatic compound is benzene.

4. The process of claims 1, 2 or 3 having the additional steps of removing water from the gas after it has passed through the reaction mass, and then recycling the gas back to the reaction mass.

* * * * *